(12) United States Patent
Li et al.

(10) Patent No.: US 8,623,780 B2
(45) Date of Patent: Jan. 7, 2014

(54) PREPARATION PROCESS OF A COMPLEX OXIDE CATALYST AND APPLICATION THEREOF TO THE SYNTHESIS OF THE ACRYLIC ACID

(75) Inventors: Xuemei Li, Shanghai (CN); Chunhua Qin, Shanghai (CN); Kun Jiao, Shanghai (CN); Shiqiang Feng, Shanghai (CN); Yan Zhuang, Shanghai (CN); Jianxue Ma, Shanghai (CN); Xiaodong Zhu, Shanghai (CN); Jingming Shao, Shanghai (CN)

(73) Assignee: Shanghai Huayi Acrylic Acid Co., Ltd., Shanghai (CN)

( * ) Notice: Subject to any disclaimer, the term of this patent is extended or adjusted under 35 U.S.C. 154(b) by 373 days.

(21) Appl. No.: 12/690,662

(22) Filed: Jan. 20, 2010

(65) Prior Publication Data

US 2010/0204513 A1 Aug. 12, 2010

(30) Foreign Application Priority Data

Feb. 10, 2009 (CN) .......................... 2009 1 0046049

(51) Int. Cl.
   *B01J 23/00* (2006.01)

(52) U.S. Cl.
   USPC ............ 502/312; 502/311; 502/248; 502/535

(58) Field of Classification Search
   USPC ................... 502/312, 311, 248, 535
   See application file for complete search history.

(56) References Cited

U.S. PATENT DOCUMENTS

| | | | | |
|---|---|---|---|---|
| 4,035,417 | A | * | 7/1977 | Izawa et al. .................... 562/535 |
| 4,892,856 | A | * | 1/1990 | Kawajiri et al. ............... 502/247 |
| 5,959,143 | A | * | 9/1999 | Sugi et al. ...................... 562/534 |
| 2005/0239643 | A1 | * | 10/2005 | Benderly et al. ............... 502/312 |
| 2008/0092502 | A1 | * | 4/2008 | Ando et al. ..................... 55/523 |

* cited by examiner

*Primary Examiner* — Colleen Dunn
*Assistant Examiner* — Haytham Soliman

(57) ABSTRACT

The present invention provides a complex oxide catalyst whose general formula is $Mo_{12}V_aCu_bW_cX_dY_eO_f/Z$. reducing agent needs to be added into the catalyst during the preparation process of the active component of the catalyst and (or) molding process of the catalyst. Specifically, X is at least one selected from a group consisting of Nb, Sb, Sr, Ba and Te; Y is at least one selected from a group consisting of La, Ce, Nd, Sm and Cs; "a" is ranging from 2 to 8; "b" is ranging from 1 to 6; "c" is ranging from 0.5 to 5; "d" is ranging from 0.01 to 4; "e" is ranging from 0.01 to 4; f is determined by the oxidation state of the component element; Z is silicon powder; the reducing agent is C2~C6 diol or polyol.

11 Claims, No Drawings

PREPARATION PROCESS OF A COMPLEX OXIDE CATALYST AND APPLICATION THEREOF TO THE SYNTHESIS OF THE ACRYLIC ACID

BACKGROUND OF THE PRESENT INVENTION

1. Field of Invention

The present invention relates to a preparation process of a complex oxide catalyst and the application of the catalyst to the synthesis of the acrylic acid by using acrolein in the presence of the molecular oxygen.

2. Description of Related Arts

It is well known that the gas phase oxidation of the acrolein in the presence of the molecular oxygen can yield acrylic acid. Especially, the complex oxide catalyst of Mo-V system for the above-mentioned gas phase oxidation has been widely studied and applied to the industries, which can yield acrylic acid efficiently. The catalyst system for the acrolein to yield acrylic acid has been improved, but there are still two more problems. One is the hot spot problem in the catalyst bed; two is the life span problem of the catalyst.

In the industry, in order to increase the yield of the target product, the concentration of the acrolein in the raw gas or the airspeed is increased. However, the tremendous heat produced during the high load oxidation reaction cause the high temperature spot in the catalyst bed. The excessive oxidation caused by the high temperature spot can decrease the selectivity and the yield of the main product. The high temperature can also easily cause the decomposition of the catalyst, which will result in the deactivation of the catalyst. Sometimes, the high temperature can also cause temperature jump. Besides, during the oxidation reaction, the deactivation of the catalyst is inevitable. Therefore, in industry, in order to assure the conversion of the acrolein, the reaction temperature needs to be increased. Lowering the initial temperature of the catalyst and reducing the difference between the hot spot temperature and the reaction temperature can help to increase the temperature range of the catalyst, so as to prolong the life span of the catalyst. Moreover, improving the activity of the catalyst can lower the initial temperature of the catalyst and prolong the life span of the catalyst, assuming that the selectivity of the main product is not lowered.

There have been many techniques to solve the hot spot problem. JP 30688 mixes inert substance with the catalyst at the entrance of the reactor. JP 10802 gradually increases the proportion of the active component of the load in the carrier from the entrance to the exit of the reactor. JP 241209 and CN 1070840 gradually reduce the size of catalyst granules disposed from the entrance to the exit of the reactor. JP 336060 discloses a method of reduce the activity of the catalyst by filling alkali metal at the entrance of the reactor. CN 1672790A discloses a method of reduce the initial activity of the catalyst by adding a kind of volatile inorganic ammonium ion as toxic material into the catalyst. CN 1266106C discloses a method of filling catalyst from low activity to high activity along the flowing of the raw gas in the reactor. The above methods can restrain the hot spot temperature to a certain degree, but because the active substance of the catalyst at the entrance of the reactor is less than that at the exit of the reactor, the catalyst at the entrance is deactivated faster than the catalyst at the exit, which will affect the stabilization of the effectiveness of the catalyst during the long-term reaction. Adding toxic components to reduce the activity of the catalyst can restrain the hot spot temperature, but will decrease the conversion of the acrolein in the early stage of the reaction, which will result in low yield; filling low active catalyst has the same problem. Furthermore, after the toxic components are attached onto the active site of the catalyst, the stability of the catalyst will be compromised after long-term oxidation reaction.

Many articles disclose how to improve the activity and the stability of the catalyst. EP427508, EP235760, JP200055, W027437, JP210991, WO9908788, CN1050779C, CN1697692A and CN1112968C disclose a method of adjusting the components of the catalyst to improve the activity and stability of the catalyst. JP847641 and JP847643 disclose that taking solid superacid having an acid strength H0≤−11.93 as carrier in the complex oxide catalyst can improve the activity and stability of the catalyst. CN1853786 discloses that taking solid superacid having an acid strength H0≤−11.93 as carrier contribute the performance of the gas phase oxidation of the acrolein. CN100345631C discloses a method of adjusting the component distribution of the catalyst from the bulk phase to surface to obtain the catalyst of the acrylic acid. JP25914 discloses a method of adding organic acid during the catalyst preparation process to improve the performance of the catalyst. However, the above-mentioned methods can not completely meet the demand of stable high yield of acrylic acid in a long term.

It is well known that the valence state of the vanadium in the oxide containing vanadium in the catalyst can affect performance of catalyst. As disclosed in CN1177763C, the valence state of V in the catalyst can greatly affect the oxidation reaction of the acrolein. When the 99% of V has a valence state of V4+, the catalyst has good performance. Therefore, adjusting the gas components for roasting catalyst can regulate the activity of the catalyst.

During the preparation of the catalyst in the present invention, C2~C6 diol or polyol is used as reducing agent that can create active phase during the roasting process to increase the activity of the catalyst and lower the initial temperature of the catalyst. The silicon power of Z component is used to remove the heat produced during the reaction in time, so as to ease the accumulation of the heat and reduce the difference between the hot spot temperature and the salt bath temperature. In the above two measures, the catalyst can increase the conversion rate and the selectivity of main product, and can operate within a wide temperature range without temperature jump, so that the stability of the catalyst is improved. The catalyst is used for the acrolein to produce acrylic acid with high selectivity and high yield, and can be applied to the stack gas recycle and non-recycle.

SUMMARY OF THE PRESENT INVENTION

An object of the present invention is to provide a preparation process of a complex oxide catalyst and the application of the catalyst to the synthesis of the acrylic acid by using acrolein in the presence of the molecular oxygen.

Accordingly, in order to accomplish the above object, the present invention provides a complex oxide catalyst whose general formula is $Mo_{12}V_aCu_bW_cX_dY_eO_f/Z$. reducing agent needs to be added into the catalyst during the preparation process of the active component of the catalyst and (or) molding process of the catalyst. Specifically, X is at least one selected from a group consisting of Nb, Sb, Sr, Ba and Te; Y is at least one selected from a group consisting of La, Ce, Nd, Sm and Cs; "a" is ranging from 2 to 8; "b" is ranging from 1 to 6; "c" is ranging from 0.5 to 5; "d" is ranging from 0.01 to 4; "e" is ranging from 0.01 to 4; f is determined by the oxidation state of the component element; Z is silicon powder; the reducing agent is C2~C6 diol or polyol.

Mo sources from molybdic acid, secondary ammonium molybdate or molybdenum oxide; V sources from ammonium metavanadate, vanadium oxide or vanadium oxalate; W sources from tungstic acid, ammonium paratungstate or ammonium metatungstate, Cu sources from copper nitrate, copper acetate or copper oxalate; X and Y source from corresponding oxides or salt or hydroxide that can be decomposed to the oxides.

The preparation process of the catalyst is illustrated as follows. Add Mo, V and W sources into water of 70 to 100° C. to obtain A solution; Add Cu, X and Y sources into water of 60 to 80° C. to obtain B solution; mix B solution with A solution to obtain C solution at 40 to 80° C.; mix Z component with the C solution to obtain D solution; dry D solution to obtain catalyst powder. Or dry C solution to obtain powder and then mix the powder with Z component to obtain catalyst powder. The reducing agent is added during the preparation of A solution, B solution, C solution, D solution or during the mixing process of the dry powder and Z component.

The weight of the reducing agent is 3% to 50% of the weight of the catalyst, and the weight of the Z component is 20% to 80% of the weight of the catalyst. The drying process is implemented in a static drying condition under 90 to 200° C. or in a spray drying condition under entrance temperature 280 to 350° C. and exit temperature 130 to 160° C. The catalyst powder is molded by adding water and adhesive agent. The weight of the adhesive agent is 0.5 to 10% of the weight of the catalyst. The molded catalyst is granules of spherical shape, or solid or hollow column shape. The catalyst is roasted under a temperature ranging from 320° C. to 480° C. for 1 to 30 hours in a gas consisting of oxygen, inert gas, reducing gas to become the final product.

The acrolein for preparing acrylic acid reacts in the presence of the molecular oxygen. The raw gas consists of 2~14% acrolein, 0.5~25% oxygen, 1~30% steam, and 15~80% inert gas. The reacting temperature is from 200~300° C.; the pressure is from normal pressure to 0.02 Mpa; the air speed is from 900 to 8000 $h^{-1}$.

The advantages are illustrated as follows. The initial temperature of the catalyst is low; the heat accumulated in the hot spot is small; there is little difference between the hot spot temperature and the salt bath temperature. The catalyst can increase the conversion rate and the selectivity of main product, and can operate within a wide temperature range without temperature jump; the stability of the catalyst is improved. The catalyst is used for the acrolein to produce acrylic acid with high selectivity and high yield, and can be applied to the stack gas recycle and non-recycle.

DETAILED DESCRIPTION OF THE PREFERRED EMBODIMENT

The present invention is further illustrated through the following embodiments, without limiting the scope of the claims.

EXAMPLE I

Add 150 g ammonium molybdate, 34.2 g ammonium paratungstate, and 40.5 g ammonium metavanadate into 700 g and 80° C. water to obtain A solution; Add 5 g barium nitrate, 2.3 g lanthanum nitrate, and 35.7 g copper nitrate into 80 g and 60° C. water to obtain B solution. Mix A solution and B solution at 60° C. to obtain C solution, and dry C solution at 120° C. for 20 h to obtain a dry powder. Mix evenly 100 g this dry powder, 85 g silicon powder, 37 g propanediol and 18.5 g silicasol (30%), and squeeze the mixture into column-shape granules of 2 mm length and 1 mm diameter. Roast the granules at 390° C. for 6 h in the air for being used as catalyst in the oxidation reaction of acrolein.

The oxidation reaction reacts in a reactor having a 20 mm inner diameter, which has a tube inside thereof having a 3 mm outer diameter. 15 ml catalyst is filled into the reactor. The raw gases are 7% acrolein, 9% oxygen, 15% vapor, 1.4% unreacted propylene and other organic compounds, and nitrogen taking up the rest volume. The airspeed is 1500 $h^{-1}$; the reaction temperature is 242° C.; the hot spot temperature is 275° C. The conversion of the acrolein is 99.5% and the acrylic acid yield of is 97.7%.

EXAMPLE II

Add 50 g glycol, 150 g ammonium molybdate, 33.8 g ammonium paratungstate, and 41.6 g ammonium metavanadate into 700 g and 80° C. water to obtain A solution; Add 3 g barium nitrate, 2.3 g lanthanum nitrate, and 35.7 g copper nitrate into 80 g and 60° C. water to obtain B solution. Mix A solution and B solution at 60° C. to obtain C solution, and dry C solution at 120° C. for 20 h to obtain a dry powder. Mix evenly 100 g this dry powder, 90 g silicon powder and 19 g silicasol (30%), and squeeze the mixture into column-shape granules of 2 mm length and 1 mm diameter. Roast the granules at 380° C. for 5 h in the air for being used as catalyst in the oxidation reaction of acrolein.

The condition of the oxidation reaction of this example is same as example I. When the reaction temperature is 241° C., the hot spot temperature is 273° C., the conversion of the acrolein is 99.1% and the acrylic acid yield of is 97.9%.

EXAMPLE III

Add 40 g propanediol, 130.2 g ammonium molybdate, 28.4 g ammonium metatungstate, and 38.1 g ammonium metavanadate into 600 g and 90° C. water to obtain A solution; Add 3 g lanthanum nitrate, 4.2 g niobium oxalate, and 38.1 g copper nitrate into 80 g and 60° C. water to obtain B solution. Mix A solution and B solution at 60° C. to obtain C solution, and dry C solution at 120° C. for 20 h to obtain a dry powder. Mix evenly 100 g this dry powder, 90 g silicon powder, 3.8 g graphite and 19 g silicasol (30%), and squeeze the mixture into column-shape granules of 2 mm length and 1 mm diameter. Roast the granules at 380° C. for 5 h in the air for being used as catalyst in the oxidation reaction of acrolein.

The condition of the oxidation reaction of this example is same as example I. When the reaction temperature is 244° C., the hot spot temperature is 278° C., the conversion of the acrolein is 99.3% and the acrylic acid yield of is 96.7%.

EXAMPLE IV

Add 50 g butanediol, 130.2 g ammonium molybdate, 28.4 g ammonium metatungstate, and 38.1 g ammonium metavanadate into 600 g and 90° C. water to obtain A solution; Add 2.6 g cerium nitrate and 38.1 g copper nitrate into 80 g and 60° C. water to obtain B solution. Mix A solution and B solution at 60° C. to obtain C solution, mix 320 g silicon powder with C solution, and dry the mixture at 150° C. for 10 h to obtain a dry powder. Mix evenly 100 g this dry powder, 1.5 g graphite and 6.5 g silicasol (30%), and squeeze the mixture into column-shape granules of 2 mm length and 1 mm diameter. Roast the granules at 390° C. for 6 h in the air for being used as catalyst in the oxidation reaction of acrolein.

The condition of the oxidation reaction of this example is same as example I. When the reaction temperature is 265° C., the hot spot temperature is 290° C., the conversion of the acrolein is 99.0% and the acrylic acid yield of is 96.5%.

EXAMPLE V

Add 20 g glycerol, 130.2 g ammonium molybdate, 28.4 g ammonium paratungstate, and 38.1 g ammonium metavanadate into 600 g and 90° C. water to obtain A solution; Add 1.8 g neodymium nitrate and 38.1 g copper nitrate into 80 g and 80° C. water to obtain B solution. Mix A solution and B solution at 70° C. to obtain C solution, mix 160 g silicon powder with C solution, and dry the mixture at 150° C. for 10 h to obtain a dry powder. Mix evenly 100 g this dry powder, 2 g graphite and 6.5 g silicasol (30%), and squeeze the mixture into column-shape granules of 2 mm length and 1 mm diameter. Roast the granules at 390° C. for 6 h in the air for being used as catalyst in the oxidation reaction of acrolein.

The condition of the oxidation reaction of this example is same as example I. When the reaction temperature is 243° C., the hot spot temperature is 276° C., the conversion of the acrolein is 99.5% and the acrylic acid yield of is 96.2%.

EXAMPLE VI

Add 30 g neopentyl glycol, 130.2 g ammonium molybdate, 28.4 g ammonium metatungstate, and 38.1 g ammonium metavanadate into 600 g and 90° C. water to obtain A solution; Add 1.8 g lanthanum nitrate, 2.3 g strontium nitrate and 38.1 g copper nitrate into 80 g and 80° C. water to obtain B solution. Mix A solution and B solution at 60° C. to obtain C solution, and dry C solution at 120° C. for 20 h to obtain a dry powder. Mix evenly 100 g this dry powder, 60 g silicon powder, 10 g silicon oxide, 3.4 g graphite and 11 g silicasol (30%), and squeeze the mixture into column-shape granules of 2 mm length and 1 mm diameter. Roast the granules at 390° C. for 6 h in the air for being used as catalyst in the oxidation reaction of acrolein.

The condition of the oxidation reaction of this example is same as example I. When the reaction temperature is 245° C., the hot spot temperature is 280° C., the conversion of the acrolein is 99.1% and the acrylic acid yield of is 97.5%.

EXAMPLE VII

The preparation of the catalyst and the condition of the oxidation reaction are same as example III. The granules are roasted at 370° C. for being used as catalyst in the oxidation reaction of acrolein. When the reaction temperature is 243° C., the hot spot temperature is 277° C., the conversion of the acrolein is 99.2% and the acrylic acid yield of is 96.1%.

EXAMPLE VIII

The preparation of the catalyst and the condition of the oxidation reaction are same as example III. The granules are roasted at 410° C. for being used as catalyst in the oxidation reaction of acrolein. When the reaction temperature is 246° C., the hot spot temperature is 277° C., the conversion of the acrolein is 99.1% and the acrylic acid yield of is 96.3%.

EXAMPLE IX

The preparation of the catalyst and the condition of the oxidation reaction are same as example III. The raw gases are 5% acrolein, 6% oxygen, 11% vapor, 1.2% unreacted propylene and other organic compounds, and nitrogen taking up the rest volume. The airspeed is 1500 h$^{-1}$; the reaction temperature is 242° C.; the hot spot temperature is 273° C. The conversion of the acrolein is 99.6% and the acrylic acid yield of is 96.7%.

EXAMPLE X

The preparation of the catalyst and the condition of the oxidation reaction are same as example III. When the reaction temperature is gradually rising from 244° C. to 264° C., the hot spot temperature is gradually rising from 278° C. to 301° C., and there is no temperature jump, the conversion of the acrolein is rising from 99.5% to 100% and the acrylic acid yield of is 96.3%.

EXAMPLE XI

Add 400 g propanediol, 1302 g ammonium molybdate, 284 g ammonium metatungstate, and 381 g ammonium metavanadate into 6000 g and 90° C. water to obtain A solution; Add 26 g lanthanum nitrate, 42 g niobium oxalate and 381 g copper nitrate into 800 g and 60° C. water to obtain B solution. Mix A solution and B solution at 60° C. to obtain C solution, and dry C solution at 120° C. for 20 h to obtain a dry powder. Mix evenly 1000 g this dry powder, 900 g silicon powder, 38 g graphite and 190 g silicasol (30%). Make the mixture into column-shape hollow granules of 3 mm length, 2 mm inner diameter and 5 mm outer diameter. Roast the granules at 380° C. for 5 h in the air for being used as catalyst in the oxidation reaction of acrolein.

The oxidation reaction reacts in a 3400 mm long reactor having a 27 mm inner diameter, which has a tube inside thereof having an 8 mm outer diameter. Fill the catalyst mixed with 30% inert particles at the entrance of the reactor, and the height of the mixture is 1000 mm; fill the 100% catalyst at the lower end of the reactor, and the height of the catalyst is 2000 mm. The raw gases are 7% acrolein, 9% oxygen, 15% vapor, 1.3% unreacted propylene and other organic compounds, nitrogen taking up the rest volume and the airspeed is 1500 h−1. After 200 hours, when the reaction temperature is 255° C., the conversion of the acrolein is 99.5% and the acrylic acid yield of is 96.6%. After 200 hours, when the reaction temperature is 255° C., the conversion of the acrolein is 99.5% and the acrylic acid yield of is 96.6%. After 9000 hours, when the reaction temperature is 258° C., the conversion of the acrolein is 99.4% and the acrylic acid yield of is 96.8%.

COMPARISON EXAMPLE I

The preparation process of the catalyst is same as Example I. Do not add lanthanum nitrate during the preparation of B solution. The condition of the oxidation reaction is same as example I. When the reaction temperature is 249° C. and the hot spot temperature is 281° C., the conversion of the acrolein is 99.0% and the acrylic acid yield of is 94.7%.

COMPARISON EXAMPLE II

The preparation process of the catalyst is same as Example IV. Do not add butanediol during the preparation of catalyst. The condition of the oxidation reaction is same as example I. When the reaction temperature is 280° C. and the hot spot temperature is 314° C., the conversion of the acrolein is 99.2% and the acrylic acid yield of is 95.0%.

COMPARISON EXAMPLE III

The preparation process of the catalyst is same as Example VI. Replace silicon oxide with silicon powder during the preparation of catalyst. The condition of the oxidation reaction is same as example I. When the reaction temperature is 245° C. and the hot spot temperature is 298° C., the conversion of the acrolein is 99.5% and the acrylic acid yield of is 93.7%.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A complex oxide catalyst used for acrolein to prepare acrylic acid, having a general formula $Mo_{12}V_aCu_bW_cX_dY_eO_f/Z$, wherein X is at least one selected from a group consisting of Nb, Sb, Sr, Ba and Te; Y is at least one selected from a group consisting of La, Ce, Nd, Sm and Cs; "a" is ranging from 2 to 8; "b" is ranging from 1 to 6; "c" is ranging from 0.5 to 5; "d" is ranging from 0.01 to 4; "e" is ranging from 0.01 to 4; f is determined by an oxidation state of the component element; Z is silicon powder, wherein a reducing agent is added during a preparation or a molding process of the catalyst, and the reducing agent is C2~C6 diol or polyol, wherein a weight of the Z component is 20% to 80% of a weight of the catalyst in a form of powder.

2. The complex oxide catalyst, as recited in claim 1, wherein Mo is selected from a group consisting of molybdic acid, secondary ammonium molybdate and molybdenum oxide; V is selected from a group consisting of ammonium metavanadate, vanadium oxide and vanadium oxalate; W is selected from a group consisting of tungstic acid, ammonium paratungstate and ammonium metatungstate, Cu is selected from a group consisting of copper nitrate, copper acetate and copper oxalate; X and Y are selected from a group consisting of corresponding oxides, or salt or hydroxide that can be decomposed to the oxides.

3. A preparation process of a catalyst according to claim 1, comprising steps of:
   adding Mo, V and W sources into water of 70 to 100° C. to obtain A solution;
   adding Cu, X and Y sources into water of 60 to 80° C. to obtain B solution;
   mixing B solution with A solution to obtain C solution at 40 to 80° C.;
   mixing Z component with the C solution to obtain D solution and drying D solution to obtain catalyst powder, or drying C solution to obtain powder and mixing the powder with Z component to obtain catalyst powder, in such a manner that a weight of the Z component is 20% to 80% of a weight of the catalyst.

4. The preparation process of a catalyst, as recited in claim 3, further comprising a step of adding reducing agent during preparation of A solution, B solution, C solution, D solution or during mixing process of the powder and Z component.

5. The preparation process of a catalyst, as recited in claim 4, wherein a weight of the reducing agent is 3% to 50% of a weight of the catalyst.

6. The preparation process of a catalyst, as recited in claim 3, wherein the drying process is implemented in a static drying condition under 90 to 200° C. or in a spray drying condition with entrance temperature 280 to 350° C. and exit temperature 130 to 160° C.

7. The preparation process of a catalyst, as recited in claim 3, further comprising a step of molding the catalyst powder by adding water and adhesive agent, wherein a weight of the adhesive agent is 0.5 to 10% of a weight of the catalyst, and the molded catalyst is granules of spherical shape, or solid or hollow column shape.

8. The preparation process of a catalyst, as recited in claim 7, wherein catalyst is roasted under a temperature ranging from 320° C. to 480° C. for 1 to 30 hours in a gas consisting of oxygen, inert gas, and reducing gas to become final product.

9. The preparation process of a catalyst, as recited in claim 3, specifically comprising:
   adding 150 g ammonium molybdate, 34.2 g ammonium paratungstate, and 40.5 g ammonium metavanadate into 700 g and 80° C. water to obtain A solution; adding 5 g barium nitrate, 2.3 g lanthanum nitrate, and 35.7 g copper nitrate into 80 g and 60° C. water to obtain B solution, mixing the A solution and the B solution at 60° C. to obtain C solution, and drying the C solution at 120° C. for 20 h to obtain a dry powder, mixing evenly 100 g the dry powder, 85 g silicon powder, 37 g propanediol and 18.5 g silicasol (30%), and squeezing the mixture into column-shape granules of 2 mm length and 1 mm diameter, and roasting the granules at 390° C. for 6 h in the air for being used as catalyst in the oxidation reaction of acrolein,
   wherein the oxidation reaction reacts in a reactor having a 20 mm inner diameter, which has a tube inside thereof having a 3 mm outer diameter, 15 ml catalyst is filled into the reactor, raw gases are 7% acrolein, 9% oxygen, 15% vapor, 1.4% unreacted propylene and other organic compounds, and nitrogen taking up the rest volume, an airspeed is 1500 h$^{-1}$; a reaction temperature is 242° C.; and a hot spot temperature is 275° C.

10. The preparation process of a catalyst, as recited in claim 3, specifically comprising:
    adding 50 g butanediol, 130.2 g ammonium molybdate, 28.4 g ammonium metatungstate, and 38.1 g ammonium metavanadate into 600 g and 90° C. water to obtain A solution; adding 2.6 g cerium nitrate and 38.1 g copper nitrate into 80 g and 60° C. water to obtain B solution, mixing the A solution and the B solution at 60° C. to obtain C solution, mixing 320 g silicon powder with the C solution, and drying the mixture at 150° C. for 10 h to obtain a dry powder, mixing evenly 100 g the dry powder, 1.5 g graphite and 6.5 g silicasol (30%), and squeezing the mixture into column-shape granules of 2 mm length and 1 mm diameter, and roasting the granules at 390° C. for 6 h in the air for being used as catalyst in the oxidation reaction of acrolein,
    wherein the oxidation reaction reacts in a reactor having a 20 mm inner diameter, which has a tube inside thereof having a 3 mm outer diameter, 15 ml catalyst is filled into the reactor, raw gases are 7% acrolein, 9% oxygen, 15% vapor, 1.4% unreacted propylene and other organic compounds, and nitrogen taking up the rest volume, an airspeed is 1500 h$^{-1}$; a reaction temperature is 265° C., and a hot spot temperature is 290° C.

11. The preparation process of a catalyst, as recited in claim 3, specifically comprising:
    adding 30 g neopentyl glycol, 130.2 g ammonium molybdate, 28.4 g ammonium metatungstate, and 38.1 g ammonium metavanadate into 600 g and 90° C. water to obtain A solution; adding 1.8 g lanthanum nitrate, 2.3 g strontium nitrate and 38.1 g copper nitrate into 80 g and 80° C. water to obtain B solution, mixing the A solution and the B solution at 60° C. to obtain C solution, and drying the C solution at 120° C. for 20 h to obtain a dry powder, mixing evenly 100 g the dry powder, 60 g silicon powder, 10 g silicon oxide, 3.4 g graphite and 11 g silicasol (30%), and squeezing the mixture into column-shape granules of 2 mm length and 1 mm diameter, roasting the granules at 390° C. for 6 h in the air for being used as catalyst in the oxidation reaction of acrolein, wherein the oxidation reaction reacts in a reactor having a 20 mm inner diameter, which has a tube inside thereof having a 3 mm outer diameter, 15 ml catalyst is filled into the reactor, raw gases are 7% acrolein, 9% oxygen, 15% vapor, 1.4% unreacted propylene and other organic compounds, and nitrogen taking up the rest volume, an airspeed is 1500 $h^{-1}$; a reaction temperature is 245° C., a hot spot temperature is 280° C.

* * * * *